United States Patent
Dehara et al.

(10) Patent No.: US 9,168,357 B2
(45) Date of Patent: Oct. 27, 2015

(54) LINEAR OBJECT MANIPULATION ASSISTING DEVICE

(76) Inventors: Makoto Dehara, Osaka (JP); Masatake Yuki, Osaka (JP)

(*) Notice: Subject to any disclaimer, the term of this patent is extended or adjusted under 35 U.S.C. 154(b) by 82 days.

(21) Appl. No.: 13/820,886

(22) PCT Filed: Apr. 17, 2012

(86) PCT No.: PCT/JP2012/060315
§ 371 (c)(1),
(2), (4) Date: Mar. 5, 2013

(87) PCT Pub. No.: WO2013/157077
PCT Pub. Date: Oct. 24, 2013

(65) Prior Publication Data
US 2013/0274792 A1    Oct. 17, 2013

(51) Int. Cl.
*A61F 11/00* (2006.01)
*A61M 25/02* (2006.01)
*A61B 17/12* (2006.01)
*A61B 19/02* (2006.01)

(52) U.S. Cl.
CPC .......... *A61M 25/02* (2013.01); *A61B 17/12113* (2013.01); *A61B 17/1214* (2013.01); *A61B 19/0256* (2013.01); *A61B 2017/12063* (2013.01)

(58) Field of Classification Search
CPC ........................................ A61F 2/013
USPC ............................. 604/533, 174, 180; 606/130
See application file for complete search history.

(56) References Cited

U.S. PATENT DOCUMENTS

| | | | |
|---|---|---|---|
| 4,224,937 A | * | 9/1980 | Gordon .......................... 604/180 |
| 4,981,475 A | * | 1/1991 | Haindl ........................... 604/174 |
| 5,334,187 A | * | 8/1994 | Fischell et al. ........... 604/102.02 |

(Continued)

FOREIGN PATENT DOCUMENTS

| | | |
|---|---|---|
| JP | 10-512177 A | 11/1998 |
| JP | 11-267226 A | 10/1999 |

(Continued)

OTHER PUBLICATIONS

International Search Report and Written Opinion of the International Searching Authority mailed May 29, 2012 for the corresponding international application No. PCT/JP2012/060315.

(Continued)

*Primary Examiner* — Richard Louis
(74) *Attorney, Agent, or Firm* — Muncy, Geissler, Olds & Lowe, P.C.

(57) ABSTRACT

A linear object manipulation assisting device is provided which allows easy manipulation of a linear object. A wire manipulation assisting device as a linear object manipulation assisting device assists manipulation of a delivery wire penetrating through a Y connector. The Y connector includes a main branch through which the delivery wire penetrates, and a side port that branches off from the main branch. A microcatheter having the delivery wire inserted therein is connected to one end of the main branch. The wire manipulation assisting device includes a fixing portion for fixing the Y connector and a placement portion attached to the fixing portion. A portion of the delivery wire that protrudes from the other end of the main branch can be manipulated with at least the first and second fingers of the right hand with the carpal portion of the right hand being placed on the placement portion.

2 Claims, 10 Drawing Sheets

(56) References Cited

U.S. PATENT DOCUMENTS

| | | | |
|---|---|---|---|
| 5,722,959 A | | 3/1998 | Bierman |
| 5,797,858 A | * | 8/1998 | Rourke ............ 600/585 |
| 5,839,016 A | * | 11/1998 | Folkins et al. ............ 399/46 |
| 6,231,547 B1 | * | 5/2001 | O'Hara ............ 604/174 |
| 2003/0120301 A1 | * | 6/2003 | Yock ............ 606/194 |
| 2005/0038453 A1 | * | 2/2005 | Raulerson ............ 606/151 |
| 2005/0059958 A1 | | 3/2005 | Lessard et al. |
| 2006/0015072 A1 | * | 1/2006 | Raulerson ............ 604/180 |
| 2006/0129103 A1 | * | 6/2006 | Bierman et al. ............ 604/174 |
| 2007/0066985 A1 | * | 3/2007 | Geitz et al. ............ 606/170 |
| 2007/0149930 A1 | * | 6/2007 | Bierman ............ 604/174 |
| 2010/0268266 A1 | * | 10/2010 | Keating et al. ............ 606/200 |

FOREIGN PATENT DOCUMENTS

| | | |
|---|---|---|
| JP | 2006-75524 A | 3/2006 |
| JP | 2010-94235 A | 4/2010 |
| WO | 97/15337 A1 | 5/1997 |

OTHER PUBLICATIONS

Makoto Dehara with the other seven people, Cerebral Aneurysm Embolization, Journal of Neuroendovascular Therapy, Japan, The Japanese Society for Neuroendovascular Therapy, Nov. 1, 2011, vol. 5, No. 4, p. 268 (Partial translation attached).

* cited by examiner

LINEAR OBJECT MANIPULATION ASSISTING DEVICE

CROSS REFERENCE TO RELATED APPLICATIONS

The present application is a U.S. national stage of PCT/JP2012/060315 filed on Apr. 17, 2012, whose Japanese national stage application is Japanese Patent Application No. 2012-537616 filed on Apr. 17, 2012, and issued on Nov. 2, 2012 as Japanese Patent No. 5124057, the disclosure of which is incorporated herein by reference.

TECHNICAL FIELD

The present invention relates to a linear object manipulation assisting device, and more particularly to a linear object manipulation assisting device for assisting manipulation of a linear object penetrating through a connector.

BACKGROUND ART

A cerebral aneurysm is an area in which a cerebral artery is partially ballooned to cause subarachnoid hemorrhage. Known treatment for a cerebral aneurysm includes, for example, coil embolization. In the treatment using coil embolization, two catheters in a double-tube structure are inserted from the femoral artery in the groin, passed through the main artery, and introduced to a cerebral aneurysm in the head. Then, for example, an embolization material such as a platinum coil is pushed into the cerebral aneurysm through the two catheters in a double-tube structure. As a result, the embolization material blocks blood from flowing into the cerebral aneurysm thereby preventing rupture of the cerebral aneurysm.

FIG. 9 is a diagram schematically showing a medical instrument 100 for use in coil embolization.

Referring to FIG. 9, medical instrument 100 includes Y connectors 110 and 120, a guiding catheter 130, a microcatheter 140, and a delivery wire 150. Microcatheter 140 and guiding catheter 130 form a double-tube catheter with guiding catheter 130 as an outer tube and microcatheter 140 as an inner tube. Guiding catheter 130 accommodates microcatheter 140. Delivery wire 150 is inserted through microcatheter 140. A coil (not shown) for embolizing a cerebral aneurysm is connected at the tip end of delivery wire 150.

Guiding catheter 130 is connected at the left end in FIG. 9 of Y connector 120. Microcatheter 140 and delivery wire 150 are inserted through the inside of Y connector 120. Microcatheter 140 is connected at the left end in FIG. 9 of Y connector 110. Delivery wire 150 is inserted through the inside of Y connector 110.

When coil embolization is performed using medical instrument 100, guiding catheter 130 is inserted into an artery of the human body until the tip end thereof reaches the vicinity of a cerebral aneurysm. Microcatheter 140 is pushed forward from the tip end of guiding catheter 130 into the cerebral aneurysm. A coil is pushed out of microcatheter 140 reaching the inside of the cerebral aneurysm and is pushed into the cerebral aneurysm.

A conventional manipulation method using medical instrument 100 shown in FIG. 9 will now be described.

Medical instrument 100 is manipulated by one or two operators. In the case where a single operator manipulates medical instrument 100 (which case is called "two hands"), the operator grips a grip portion 161 in the vicinity of the right end in FIG. 9 of Y connector 120 with the left hand while gripping a grip portion 162 in the vicinity of the right end in FIG. 9 of Y connector 110 with the right hand. The operator manipulates advancement/retraction of microcatheter 140 while gripping Y connector 120 with the left hand. On the other hand, the operator manipulates advancement/retraction of delivery wire 150 while gripping Y connector 110 with the right hand.

In the case where two operators manipulate medical instrument 100 (which case is called "four hands"), an operator manipulates advancement/retraction of delivery wire 150 with the right hand while gripping Y connector 110 with the left hand. Another operator, who is an assistant, manipulates advancement/retraction of microcatheter 140 with the right hand while gripping Y connector 120 with the left hand.

A conventional method of manipulating a medical instrument for use in coil embolization is disclosed, for example, in Patent Document 1 below. Patent Document 1 discloses an insertion device operated to insert a delivery wire into a human body through a blood vessel. The insertion device includes a foot switch for generating and outputting a signal to control starting/stopping a drive device moving the delivery wire in its longitudinal direction, an insertion force sensor operative to measure longitudinally compressive force exerted to the delivery wire, and a speaker and a display for informing an operator of the compressive force measured by the insertion force sensor.

PRIOR ART DOCUMENTS

Patent Documents

Patent Document 1: Japanese Patent Laying-Open No. 2010-94235

SUMMARY OF THE INVENTION

Problems to be Solved by the Invention

When coil embolization is performed using medical instrument 100, delivery wire 150 is inserted by minutely changing the position of the tip end of microcatheter 140 and the force applied thereto. Therefore, delicate manipulation of delivery wire 150 is required. However, in the conventional manipulation method above, it is difficult to manipulate the delivery wire. In case of a mistake in manipulating the delivery wire, the delivery wire may deviate from the cerebral aneurysm or the cerebral aneurysm may be damaged. Thus, the problem is serious.

FIG. 10 is a diagram schematically showing the right hand in a case where a single operator manipulates medical instrument 100. In FIG. 10, a portion of medical instrument 100 that is hidden by the right hand is shown by a dotted line.

Referring to FIG. 10, for example, in the case where a single operator manipulates medical instrument 100, while the operator holds Y connector 110 with the first to third fingers of the right hand, the operator manipulates advancement/retraction of delivery wire 150 with the fourth and fifth fingers. Therefore, the delicate manipulation of delivery wire 150 has to be performed only with the four and fifth fingers of the right hand. In the case where an operator and an assistant manipulate medical instrument 100, the assistant manipulates microcatheter 140 in harmony with the operator manipulating delivery wire 150. Thus, the assistant is required to fully understand the operator's intention and keep perfect coordination with the operator.

The technique in Patent Document 1 requires a structure including a sensor for measuring longitudinally compressive force exerted on the delivery wire, and a speaker and a display for informing the operator of the compressive force, which leads to complication of the device structure.

The problem above is not unique to coil embolization using medical instrument 100 but may generally arise when a linear object including a delivery wire is manipulated.

The present invention is made in order to solve the problem above. An object of the present invention is to provide a linear object manipulation assisting device that allows easy manipulation of a linear object.

Another object of the present invention is to provide a linear object manipulation assisting device that allows manipulation of a linear object with a simple structure.

Means for Solving the Problems

A linear object manipulation assisting device according to an aspect of the present invention assists manipulation of a linear object penetrating through a connector. The connector includes a main tube portion through which the linear object penetrates, and a branch tube portion that branches off from the main tube portion. A catheter having the linear object inserted therein is connected to one end of the main tube portion. The linear object manipulation assisting device includes a fixing portion for fixing the connector and a placement portion attached to the fixing portion. A portion of the linear object that protrudes from the other end of the main tube portion can be manipulated with at least first and second fingers of a right hand with a carpal portion of the right hand being placed on the placement portion.

In the linear object manipulation assisting device, preferably, the placement portion includes a groove portion formed at a bottom surface thereof In the linear object manipulation assisting device, preferably, the fixing portion includes a main tube fixing portion for catching the main tube portion.

Effects of the Invention

According to the present invention, a linear object manipulation assisting device is provided which allows easy manipulation of a linear object. According to the present invention, a linear object manipulation assisting device is provided which allows manipulation of a linear object with a simple structure.

MODES FOR CARRYING OUT THE INVENTION

In the following, embodiments of the present invention will be described based on the drawings.

Figure 1:
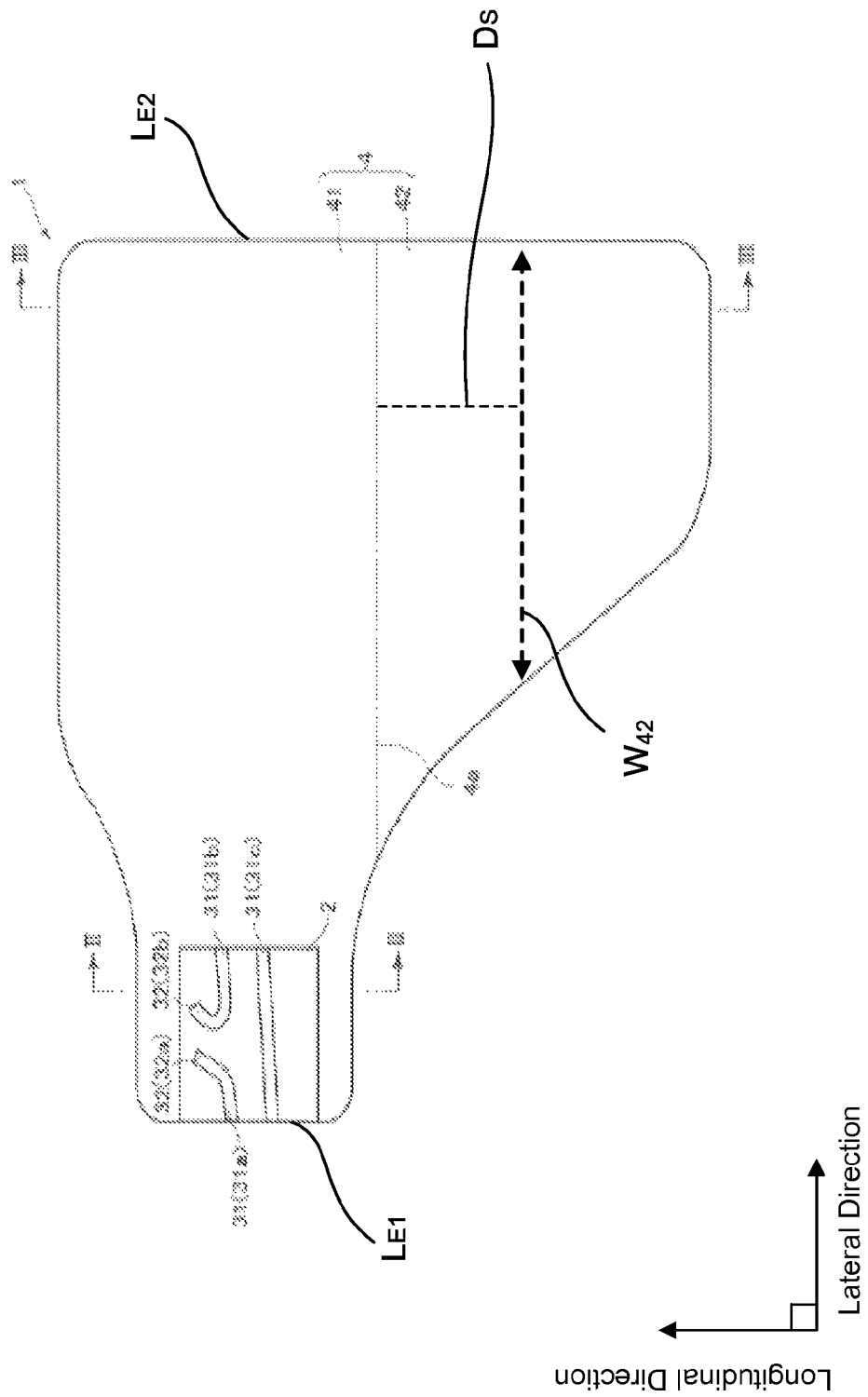
FIG. 1 is a plan view schematically showing a structure of a wire manipulation assisting device 1 according to an embodiment of the present invention.

FIG. 1 is a plan view schematically showing a structure of a wire manipulation assisting device 1 according to an embodiment of the present invention.

Referring to FIG. 1, wire manipulation assisting device 1 as a linear object manipulation assisting device in the present embodiment fixes a Y connector (an example of a connector) thereby to assist manipulation of a delivery wire (an example of the linear object) penetrating through the Y connector. Wire manipulation assisting device 1 is made of a flexible material such as plastics as a whole and includes a fixing portion 2 for fixing the Y connector and a placement portion 4 attached to fixing portion 2.

Placement portion 4 is a portion on which the carpal portion of the right hand of the operator is placed and which extends from the bottom of fixing portion 2. Preferably, the length of placement portion 4 extending from fixing portion 2 is equal to or longer than 100 mm and is equal to or shorter than 250 mm. When the length of placement portion 4 extending from fixing portion 2 is equal to or longer than 100 mm, the carpal portion of the right hand of the operator can be easily placed thereon. When the length of placement portion 4 extending from fixing portion 2 is equal to or shorter than 250 mm, the operability of wire manipulation assisting device 1 is improved.

Placement portion 4 includes a first portion 41 and a second portion 42. First portion 41 and second portion 42 are separated from each other by a straight line 4a extending laterally in FIG. 1.

First portion 41 has a shape extending from fixing portion 2 in the rightward direction in FIG. 1. The length (the longitudinal direction in FIG. 1) of first portion 41 in the vicinity of fixing portion 2 (the left end portion in FIG. 1) is shorter than the length of the other portion of first portion 41.

Second portion 42 extends from first portion 41 in the forward direction in FIG. 1 (the downward direction in FIG. 1). Second portion 42 has its width (the length in the lateral direction in FIG. 1) reduced as the distance from straight line 4a increases.

Figure 2:
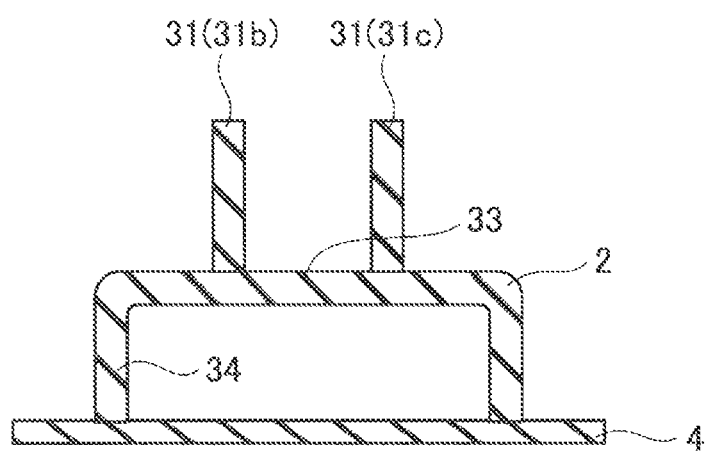
FIG. 2 is a cross-sectional view taken along a line II-II in FIG. 1.

FIG. 2 is a cross-sectional view taken along a line II-II in FIG. 1.

Referring to FIG. 1 and FIG. 2, fixing portion 2 is a portion for fixing the Y connector and includes a main tube fixing portion 31, a branch tube fixing portion 32, a Y connector placement portion 33, and two leg portions 34. Each of the two leg portions 34 extends upward from placement portion 4. Y connector placement portion 33 extends approximately parallel to placement portion 4 and couples the upper ends of the two leg portions 34 with each other. The upper surface of Y connector placement portion 33 is located higher than the upper surface of placement portion 4. Each of main tube fixing portion 31 and branch tube fixing portion 32 extends upward from Y connector placement portion 33.

Main tube fixing portion 31 includes wall portions 31a to 31c. Wall portions 31a and 31b, and wall portion 31c are parallel with each other and extend laterally in FIG. 1. There is a gap between wall portions 31a and 31b.

Branch tube fixing portion 32 includes wall portions 32a and 32b. Wall portion 32a and wall portion 32b are parallel with each other and extend from the upper right toward the lower left in FIG. 1. Wall portion 32a connects to wall portion 31a, and wall portion 32b connects to wall portion 31b.

Figure 3:
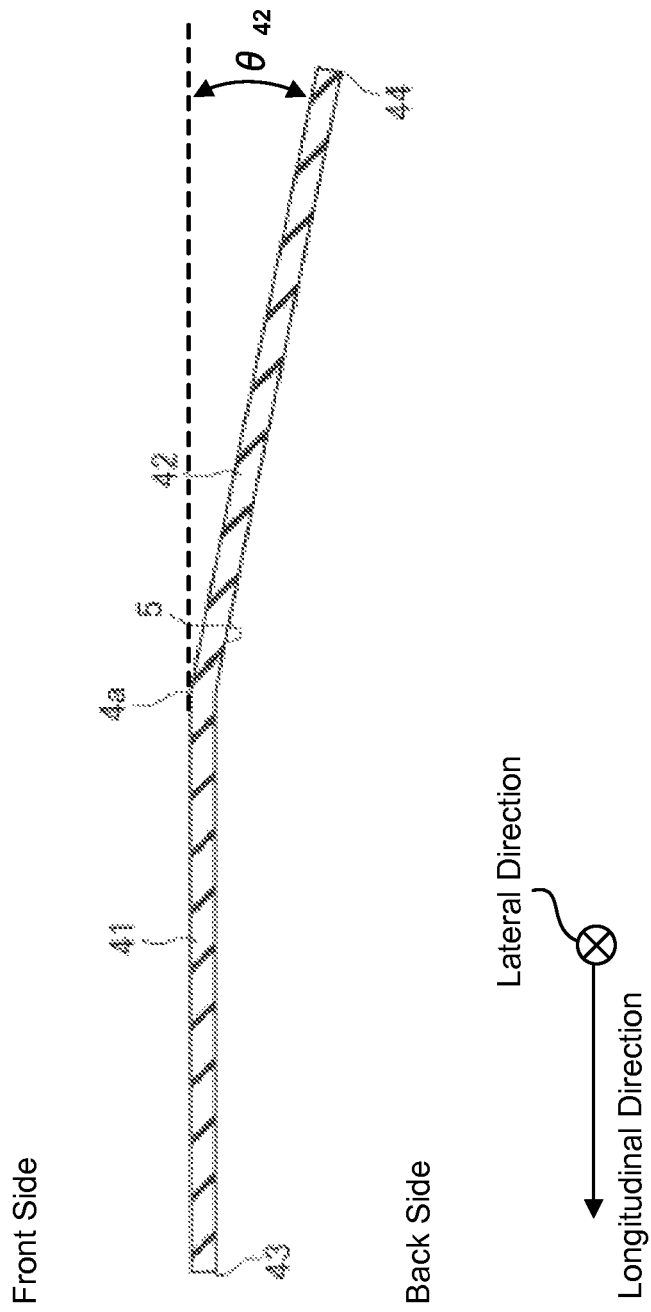
FIG. 3 is a cross-sectional view taken along a line III-III in FIG. 1.

FIG. 3 is a cross-sectional view taken along a line III-III in FIG. 1.

Referring to FIG. 1 and FIG. 3, placement portion 4 is bent with straight line 4a as a bend line. Thus, when placement portion 4 is arranged on a plane, end portions 43 and 44 of placement portion 4 are in contact with the plane, and a groove portion 5 is formed at the bottom surface of placement portion 4.

A structure of the Y connector fixed to wire manipulation assisting device 1 will now be described in detail.

Figure 4:
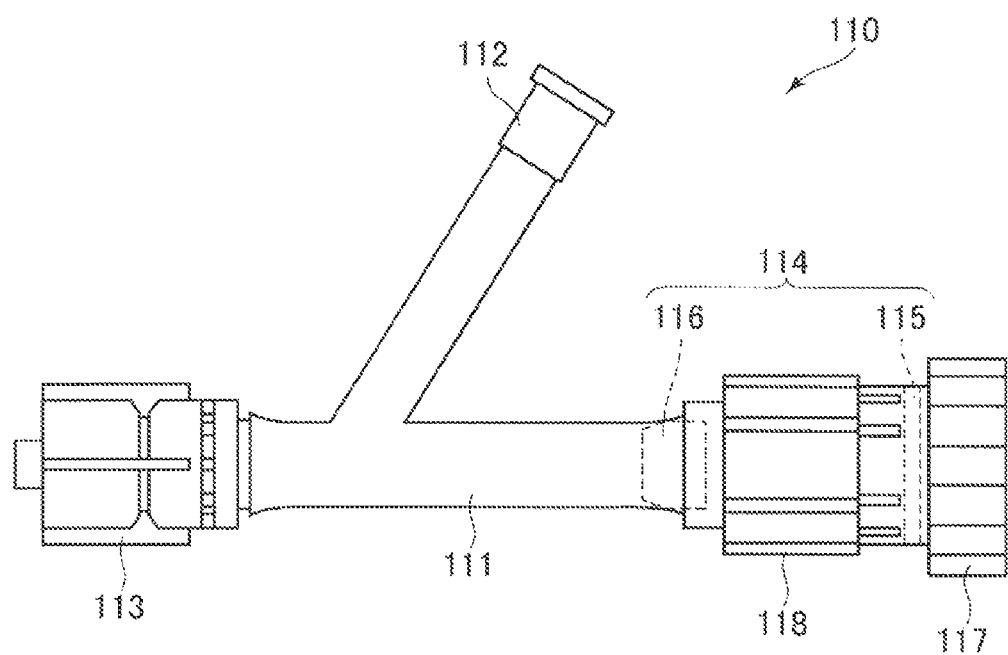
FIG. 4 is a plan view schematically showing a structure of a Y connector 110.

FIG. 4 is a plan view schematically showing a structure of a Y connector 110.

Referring to FIG. 4, Y connector 110 includes a main branch 111 (an example of the main tube portion), a side port 112 (an example of the branch tube portion), a rotator 113, a thumbwheel 114, an opener 117, and a screw 118.

Rotator 113 is attached to one end of main branch 111. Screw 118 and opener 117 are attached to the other end of main branch 111. Main branch 111, rotator 113, opener 117, and screw 118 all have a cylindrical shape to allow a deliver wire to pass through.

Side port 112 has a cylindrical shape. Side port 112 branches off from main branch 111 and is connected to main branch 111 at the lower end thereof. Liquid such as contrast medium or medication can be injected into a microcatheter through an opening at the upper end of side port 112. The liquid injected into the microcatheter passes through the inside of the microcatheter and is supplied into the patient's body.

One end of the microcatheter can be connected to rotator 113. Rotator 113 is rotatable with respect to main branch 111. The angle of the microcatheter can be changed by rotating rotator 113.

Thumbwheel 114 includes a hemostatic valve 115 and a fixed valve 116. Hemostatic valve 115 and fixed valve 116 are present in the inside of main branch 111 and therefore shown by a dotted line in FIG. 4.

Opener 117 can move along the direction in which main branch 111 extends (the lateral direction in FIG. 4). When opener 117 is pushed toward hemostatic valve 115, hemostatic valve 115 is opened. When opener 117 is pushed in the direction opposite to hemostatic valve 115, hemostatic valve 115 is closed. When opener 117 is rotated clockwise while being kept pushed toward hemostatic valve 115, hemostatic valve 115 is locked in the open state.

Screw 118 is rotatable with respect to main branch 111. When screw 118 is rotated clockwise, fixed valve 116 is closed. When screw 118 is rotated counterclockwise, fixed valve 116 is opened. When liquid is injected from side port 112, fixed valve 116 is closed to prevent leakage of the liquid from opener 117.

A method of fixing Y connector 110 to wire manipulation assisting device 1 will now be described.

Figure 5:
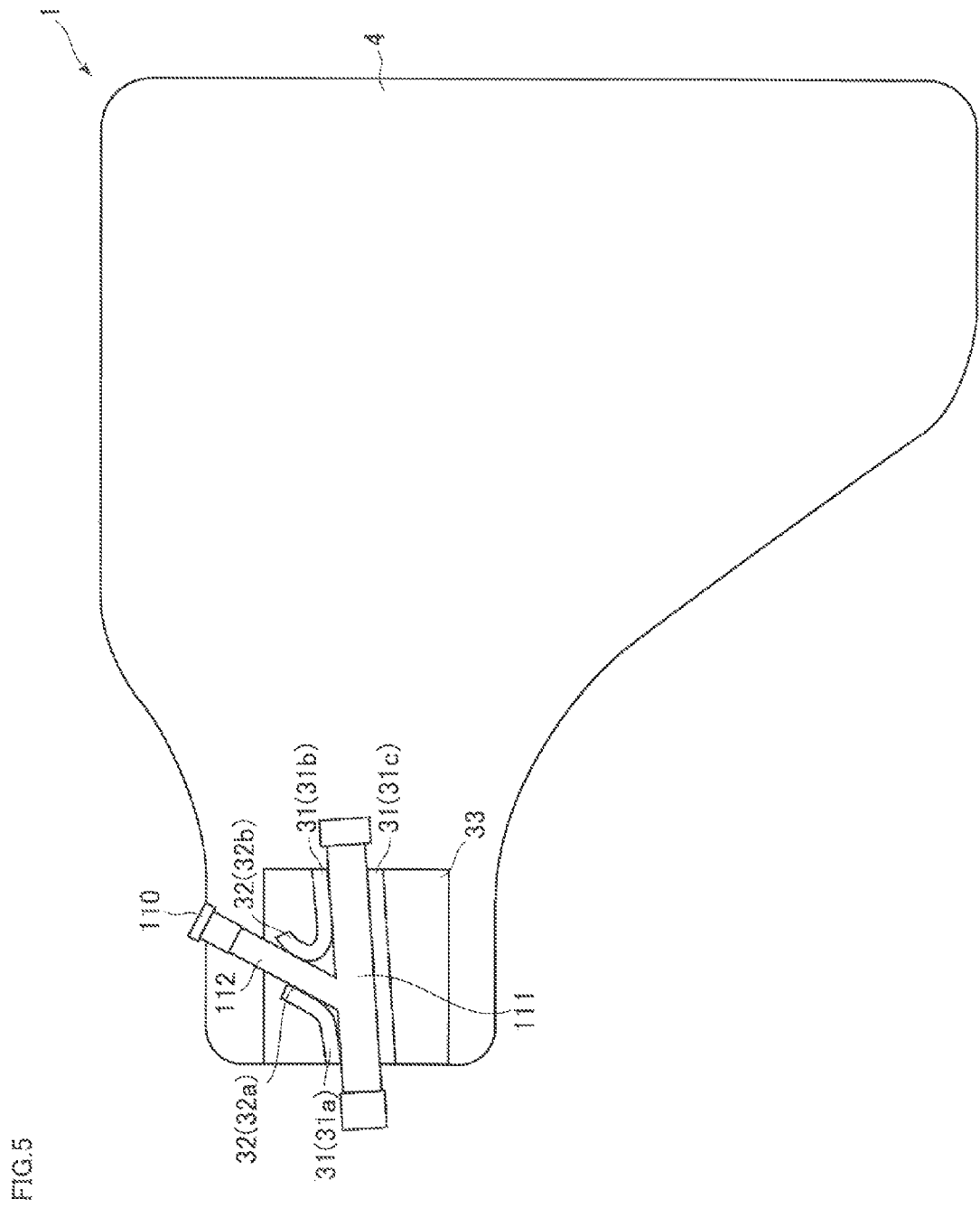
FIG. 5 is a plan view schematically showing Y connector 110 fixed to wire manipulation assisting device 1.

FIG. 5 is a plan view schematically showing Y connector 110 fixed to wire manipulation assisting device 1.

Referring to FIG. 5, first, wire manipulation assisting device 1 is arranged on a plane. Then, Y connector 110 is placed on Y connector placement portion 33 by fitting Y connector 110 into main tube fixing portion 31 and branch tube fixing portion 32 from above. The distance between wall portions 31a and 31b, and wall portion 31c is slightly smaller than the outer diameter of main branch 111 of Y connector 110. Therefore, when Y connector 110 is fitted between wall portions 31a and 31b, and wall portion 31c, the distance between wall portions 31a and 31b, and wall portion 31c is increased by Y connector 110, resulting in elastic force acting on wall portions 31a to 31c. Y connector 110 is caught by this elastic force and fixed on Y connector placement portion 33. Here, Y connector 110 may be caught additionally by the elastic force of wall portions 32a and wall portion 32b of branch tube fixing portion 32 and fixed on Y connector placement portion 33.

A method of manipulating a medical instrument 100 will now be described.

Figure 6:
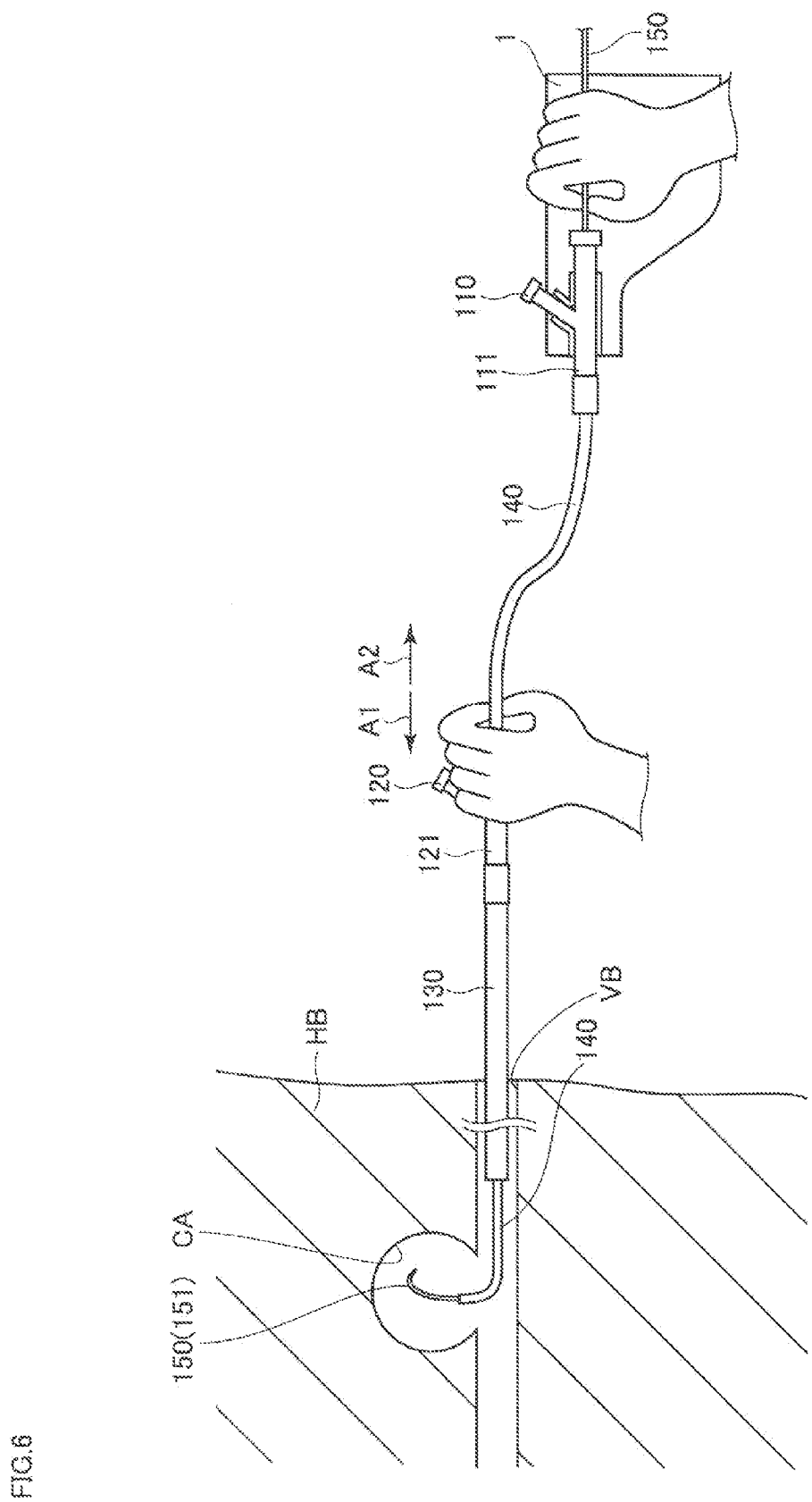
FIG. 6 is a plan view schematically showing a method of manipulating a medical instrument 100 according to an embodiment of the present invention.

FIG. 6 is a plan view schematically showing a method of manipulating medical instrument 100 according to an embodiment of the present invention.

Referring to FIG. 6, after Y connector 110 is fixed to wire manipulation assisting device 1, a guiding catheter 130 and a microcatheter 140 in a double-tube structure (an example of the catheter) and a guide wire (not shown) used to guide guiding catheter 130 and microcatheter 140 to a target site are inserted into the femoral artery VB of the human body HB. Here, microcatheter 140 is inserted in guiding catheter 130, and the guide wire is inserted in Y connector 110 and microcatheter 140. The back end of microcatheter 140 is connected to one end of main branch 111 of Y connector 110. The back end of guiding catheter 130 is connected to one end of main branch 121 of Y connector 120.

When the tip end of microcatheter 140 is introduced by the guide wire and reaches the inside of a cerebral aneurysm CA, the guide wire is pulled out of microcatheter 140, and delivery wire 150 having a coil 151 at the tip end thereof is inserted into microcatheter 140 in place of the guide wire. Delivery wire 150 is inserted in guiding catheter 130 and microcatheter 140 and penetrates through main branch 111 of Y connector 110 and main branch 121 of Y connector 120.

Next, coil 151 is retained in cerebral aneurysm CA, and current is fed between delivery wire 150 and human body HB. Coil 151 and delivery wire 150, both of which are made of an electrolytic material, are detached by passage of current. As a result, coil 151 is retained in cerebral aneurysm CA.

After cerebral aneurysm CA is filled with coil 151, guiding catheter 130, microcatheter 140, and delivery wire 150 are drawn from human body HB. Through the process above, coil embolization of cerebral aneurysm CA is completed.

In the present embodiment, medical instrument 100 is manipulated by a single operator. The operator manipulates a portion of microcatheter 140 that protrudes from the right end in FIG. 6 of main branch 121 of Y connector 120, with the first and second fingers of the left hand while gripping Y connector 120 with the third to fifth fingers of the left hand. To advance microcatheter 140, the operator moves microcatheter 140 in the direction shown by an arrow A1. To retract microcatheter 140, the operator moves microcatheter 140 in the direction shown by an arrow A2.

Figure 7:
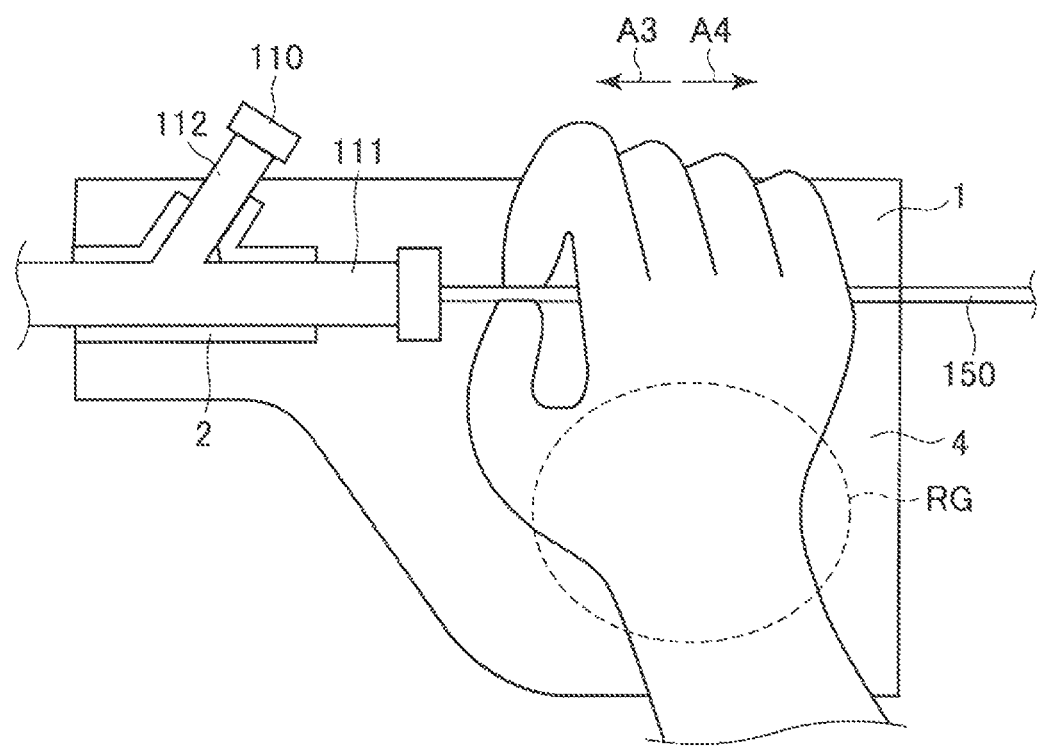
FIG. 7 is an enlarged view around wire manipulation assisting device 1 in FIG. 6.

FIG. 7 schematically shows the right hand in the case where the operator manipulates medical instrument 100.

Referring to FIG. 7, the operator places the carpal portion of the right hand on placement portion 4 of wire manipulation assisting device 1 and presses a region RG (a region surrounded by a dotted line) in placement portion 4 with the carpal portion on of the right hand. Y connector 110 thus rests on a desired position. The operator manipulates a portion of delivery wire 150 that protrudes from the right end in FIG. 7 of main branch 111 of Y connector 110 with the first and second fingers of the right hand while the carpal portion of the right hand is placed on placement portion 4. The operator may manipulate delivery wire 150 additionally using the third to fifth fingers of the right hand, if necessary. To advance deliver wire 150, the operator moves delivery wire 150 in the direction shown by an arrow A3. To retract delivery wire 150, the operator moves delivery wire 150 in the direction shown by an arrow A4.

The operator may shift wire manipulation assisting device 1 to assist advancement/retraction of microcatheter 140. To advance microcatheter 140 with delivery wire 150 being stopped, the operator arrange Y connector 120, microcatheter 140, Y connector 110, and delivery wire 150 on a straight line, removes the carpal portion of the right hand from placement portion 4 of wire manipulation assisting device 1, and grips and fixes only delivery wire 150 with the right hand. Then, the operator advances microcatheter 140 in the direction shown by the arrow A1 with the left hand. This allows Y connector 110 and wire manipulation assisting device 1 to advance in the direction shown by the arrow A3 and to follow microcatheter 140 easily.

Furthermore, the operator can advance microcatheter 140 with delivery wire 150 being stopped, by moving microcatheter 140 with the left hand in the direction shown by the arrow A1 and moving delivery wire 150 with the right hand in the direction shown by the arrow A4. The operator can advance delivery wire 150 with microcatheter 140 being stopped, by stopping microcatheter 140 with the left hand and moving delivery wire 150 with the right hand in the direction shown by the arrow A3.

[Effects of Embodiment]

According to the foregoing embodiment, the operator can easily manipulate a delivery wire (linear object) with the right hand and thus can manipulate a microcatheter or the like with the left hand simultaneously with manipulation with the right hand. As a result, a single operator can alone manipulate a medical instrument including a catheter. According to the foregoing embodiment, the delivery wire can be manipulated easily because the delivery wire is manipulated with the first and second fingers of the right hand, which have the greatest sensitivity among human fingers and make the most skillful motion. In addition, the operator and the assistant are no longer required to move in perfect coordination because the operator alone can manipulate a delivery wire and a microcatheter easily. Moreover, a delivery wire can be manipulated with a simple structure because a structure including a sensor for measuring longitudinal compressive force exerted on a delivery wire, and a speaker and a display for informing the operator of the compressive force is not necessary.

When the placement portion includes a groove portion formed at the bottom surface, friction between the placement portion and the plane on which the placement portion is arranged is reduced, so that the wire manipulation assisting device can be easily shifted.

When the fixing portion includes the main tube fixing portion that catches the main branch of the Y connector, removal/attachment of the Y connector becomes easy.

[Others]

The fixing portion may have any structure as long as it fixes the connector. In addition to the structure as in the forgoing embodiment in which the main tube portion of the connector is caught by elastic force of the main tube fixing portion, the main tube portion of the connector may be caught and fixed using spring elasticity, or the main tube portion of the connector may be anchored using a string or the like. The wire manipulation assisting device may be integrated with the Y connector. It is preferable that the wire manipulation assisting device should be discarded after use in terms of infection prevention.

Figure 8:
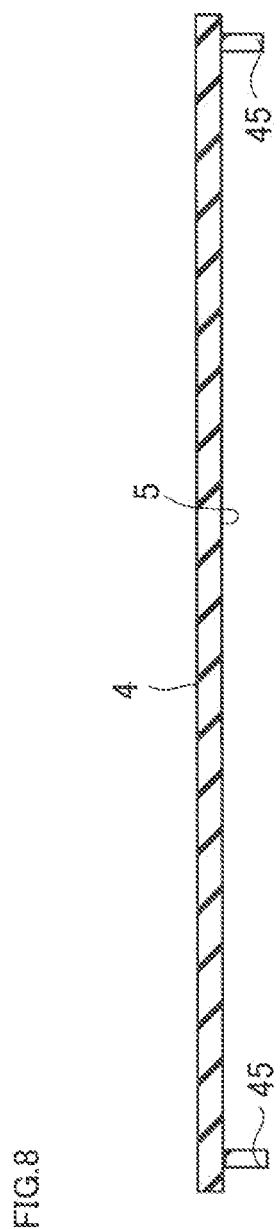
FIG. 8 is a cross-sectional view schematically showing a structure of a modification of a placement portion 4.
Figure 9:
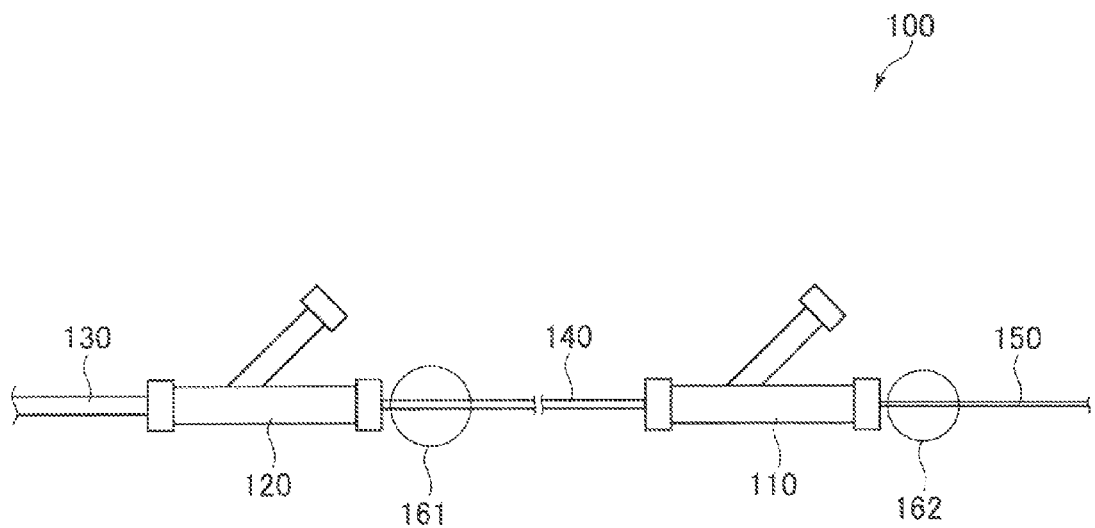
FIG. 9 is a diagram schematically showing medical instrument 100 for use in coil embolization.
Figure 10:
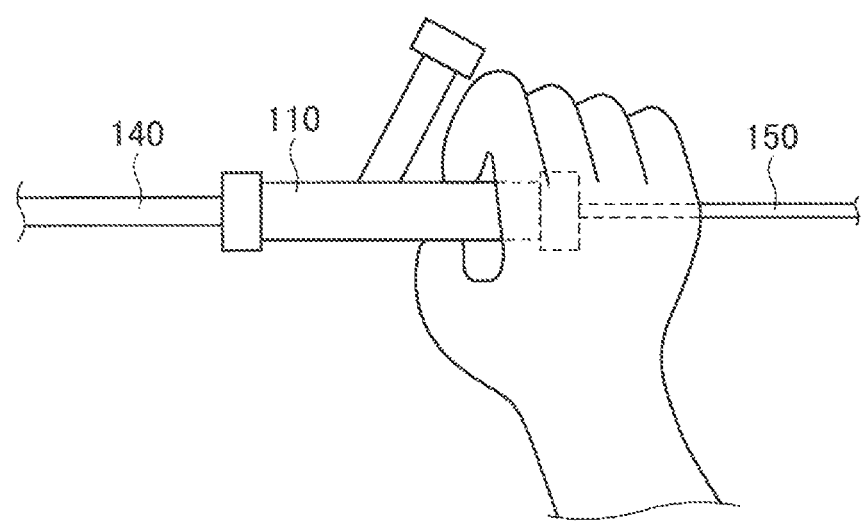
FIG. 10 is a diagram schematically showing the right hand in a case where a single operator manipulates medical instrument 100.

In addition to the case where a groove is formed at the bottom surface of the placement portion by bending the placement portion, groove portion 5 may be formed by providing leg portions 45 at the bottom surface of placement portion 4, as shown in FIG. 8.

The linear object may be a delivery wire as in the foregoing embodiment, or a guide wire or a catheter as long as it penetrates through the main tube portion.

The linear object manipulation assisting device may be applied to a medical instrument for use in a process other than coil embolization of a cerebral aneurysm and is applicable, for example, to a medical instrument including a balloon catheter, a medical instrument including an intracardiac catheter, a medical instrument including a pulmonary artery catheter, or the like.

The embodiments disclosed here should be understood as being illustrative rather than being limitative in all respects. The scope of the present invention is shown not in the foregoing description but in the claims, and it is intended that all modifications that come within the meaning and range of equivalence to the claims are embraced here.

DESCRIPTION OF THE REFERENCE SIGNS 1 wire manipulation assisting device
2 fixing portion
4 placement portion
4a straight line
5 groove portion
31 main tube fixing portion
31a to 31c wall portion of the main tube fixing portion
32 branch tube fixing portion
32a, 32b wall portion of the branch tube fixing portion
33 Y connector placement portion
34, 45 leg portion
41, 42 portion of the placement portion
43, 44 end portion of the placement portion
100 medical instrument
110, 120 Y connector
111, 121 main branch
112 side port
113 rotator
114 thumbwheel
115 hemostatic valve
116 fixed valve
117 opener
118 screw
130 guiding catheter
140 microcatheter
150 delivery wire
151 coil
161, 162 grip portion
CA cerebral aneurysm
HB human body
VB femoral artery

The invention claimed is:

1. A linear object manipulation assisting device applied to a medical instrument for assisting manipulation of a linear object which is a delivery wire penetrating through a Y connector, said Y connector including a main tube portion through which a linear object which is a delivery wire penetrates, and a branch tube portion that branches off from said main tube portion, wherein a catheter having said linear object which is the delivery wire inserted therein is connected to one end of said main tube portion, said linear object manipulation assisting device comprising:

a fixing portion for fixing said Y connector; and a placement portion attached to said fixing portion, the placement portion having a plate shape for placing a carpal portion of a right hand, wherein a portion of the linear object which is the delivery wire that protrudes from the other end of said main tube portion can be manipulated with at least first and second fingers of the right hand with the carpal portion of the right hand being placed on said placement portion, said placement portion extends from said fixing portion longer to one side of said fixing portion than to the other side of said fixing portion along an extending direction of said Y connector fixed by said fixing portion, said placement portion is configured with a first portion and a second portion that are arranged in a longitudinal direction, which is a direction perpendicular to the extending direction of said Y connector fixed by said fixing portion, each of which has a plate shapes a width (W42) of the second portion, which is measured in the extending direction of said Y connector, decrease decreases as a distance from a straight line located between said first and second portions increases, said fixing portion includes a main tube fixing portion, a branch tube fixing portion, a Y connector placement portion, and leg portions, said leg portions extends upward from said placement portion, said Y connector placement portion extends approximately parallel to said placement portion and couples the upper ends of the leg portions with each other, an upper surface of said Y connector placement portion is located higher than the upper surface of said placement portion, each of said main tube fixing portion and said branch tube fixing portion extends upward from said Y connector placement portion, said main tube fixing portion includes wall portions which are parallel with each other, said branch tube fixing portion includes wall portions which are parallel with each other, a distance between said wall portions of said main tube fixing portion is configured to be slightly smaller than the outer diameter of said main tube portion of said Y connector, so that the distance between said wall portions of said main tube fixing portion is configured to be increased by said Y connector, when said Y connector is fitted between said wall portions of said main tube fixing portion, resulting in elastic force acting on said wall portions of said main tube fixing portion and said Y connector is caught by this elastic force and elastic force of said wall portions of said branch tube fixing portion, and fixed on said Y connector placement portion, said placement portion includes a groove portion formed at a bottom surface thereof, and the second portion contacts the first portion with a predetermined angle (0Oz) so that the groove portion, which is a corner, is formed at the straight line.

2. A linear object manipulation assisting device for assisting manipulation of a linear object which is a delivery wire penetrating through a Y connector, the Y connector including a main tube portion through which a linear object which is a delivery wire penetrates, and a branch tube portion that branches off from the main tube portion, wherein a catheter having the linear object which is the delivery wire inserted therein is connected to one end of the main tube portion, the linear object manipulation assisting device comprising: a fixing portion for fixing the Y connector; and a placement portion configured with a first portion and a second portion each of which has a plate shape, the first portion and the second portion being arranged in a longitudinal direction, a lower edge of the first portion being connected to an upper edge of the second portion, wherein the fixing portion is attached on a front side of the first portion and close to one lateral end (LE1) of the placement portion, the second portion is positioned close to the other lateral end (LE2) of the placement portion, inclining toward a back side, which is opposite to the front side, with a predetermined acute angle (042) with respect to the first portion, the second portion has a width (W42) that is measured in a lateral direction, which is perpendicular to the longitudinal direction, the width (W42) being large enough for a user to place its carpal portion on the second portion so that a portion of the linear object which is the delivery wire that protrudes from the other end of said main tube portion is manipulated with a thumb and one of index and middle figures of the user above the first portion while the carpal portion of the user is placed on the second portion, said fixing portion includes a main tube fixing portion, a branch tube fixing portion, a Y connector placement portion, and leg portions, said leg portions extends upward from said placement portion, said Y connector placement portion extends approximately parallel to said placement portion and couples the upper ends of the leg portions with each other, an upper surface of said Y connector placement portion is located higher than the upper surface of said placement portion, each of said main tube fixing portion and said branch tube fixing portion extends upward from said Y connector placement portion, said main tube fixing portion includes wall portions which are parallel with each other, said branch tube fixing portion includes wall portions which are parallel with each other, a distance between said wall portions of said main tube fixing portion is configured to be slightly smaller than the outer diameter of said main tube portion of said Y connector, so that the distance between said wall portions of said main tube fixing portion is configured to be increased by said Y connector, when said Y connector is fitted between said wall portions of said main tube fixing portion, resulting in elastic force acting on said wall portions of said main tube fixing portion and said Y connector is caught by this elastic force and elastic force of said wall portions of said branch tube fixing portion, and fixed on said Y connector placement portion, the first portion is longer than the second portion in the lateral direction, the width (W4) of the second portion decreases as a distance (Ds) from the first portion increases, and a boundary between the first and second portions forms a straight line on the back side.

* * * * *